(12) United States Patent
Min et al.

(10) Patent No.: US 7,413,735 B2
(45) Date of Patent: Aug. 19, 2008

(54) PHARMACEUTICAL COMPOSITION COMPRISING ARGININE DEIMINASE FOR INHIBITING ANGIOGENESIS

(75) Inventors: Bon-Hong Min, Hanam-si (KR); Myung-Ok Park, Seoul (KR); Min-Young Kim, Daejeon (KR); Byung-Young Park, Daejeon (KR); Boe-Gwun Chun, Seongnam-si (KR); Sang-Wook Kang, Seoul (KR); Chang-Hee Moon, Daejeon (KR)

(73) Assignee: Angio Lab, Inc. (KR)

( * ) Notice: Subject to any disclaimer, the term of this patent is extended or adjusted under 35 U.S.C. 154(b) by 334 days.

(21) Appl. No.: 11/159,428

(22) Filed: Jun. 20, 2005

(65) Prior Publication Data

US 2006/0002915 A1    Jan. 5, 2006

(51) Int. Cl.
*A61K 38/00*   (2006.01)
*A61K 39/02*   (2006.01)
*C12N 9/88*    (2006.01)
*C12N 9/06*    (2006.01)
*C12N 15/70*   (2006.01)
*C12P 21/06*   (2006.01)
*C12Q 1/34*    (2006.01)
*C07H 21/04*   (2006.01)

(52) U.S. Cl. .................. 424/94.5; 435/232; 435/191; 435/18; 435/69.1; 435/320.1; 536/23.2

(58) Field of Classification Search .............. 435/183, 435/191, 232, 69.1, 320.1; 424/94.5, 190.1; 536/23.2
See application file for complete search history.

(56) References Cited

U.S. PATENT DOCUMENTS 6,183,738 B1 * 2/2001 Clark ..................... 424/94.4
6,506,730 B1 * 1/2003 Lee et al. ................. 514/12

OTHER PUBLICATIONS

Ohno et al. Cloning and nucleotide sequence of the gene encoding arginine deiminase of *Mycoplasma arginini*. Infect Immun. Nov. 1990;58(11):3788-95.*
Misawa et al. High-level expression of *Mycoplasma arginine* deiminase in *Escherichia coli* and its efficient renaturation as an anti-tumor enzyme, J Biotechnol. Aug. 15, 1994;36(2):145-55.*
Branden et al. Introduction to protein structure, Gerald Publishing Inc., New York, p. 247, 1991.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Seffernick et al. Melamine deaminase and atrazine chlorohydrolase: 98 percent identical but functionally different, J Bacteriol. Apr. 2001;183(8):2405-10.*

* cited by examiner

*Primary Examiner*—Nashaat T. Nashed
*Assistant Examiner*—Iqbal Chowdhury
(74) *Attorney, Agent, or Firm*—Baker & Hostetler, LLP

(57) ABSTRACT

The present invention relates to a pharmaceutical composition for inhibiting angiogenesis which comprises arginine deiminase as an active ingredient, where the arginine deiminase, obtained from *Mycoplasma arginini* or prepared by a genetic recombination technique, may be conjugated to an activated polymer to lower its immunogenecity and increase its life time. The pharmaceutical composition of the present invention exhibits an excellent inhibitory activity against angiogenesis.

9 Claims, 13 Drawing Sheets

FIG. 6

| | | | | | | | | | | | | | | | | |
|---|---|---|---|---|---|---|---|---|---|---|---|---|---|---|---|---|
|ATG|TCT|GTT|TTT|GAT|TCT|AAA|TTT|AAA|GGA|ATT|CAC|GTT|TAT|TCA|GAA|ATT|51
|M|S|V|F|D|S|K|F|K|G|I|H|V|Y|S|E|I|17
|GGT|GAA|TTA|GAA|TCA|GTT|CTA|GTT|CAC|GAA|CCA|GGA|CGC|GAA|ATT|GAC|TAT|102
|G|E|L|E|S|V|L|V|H|E|P|G|R|E|I|D|Y|34
|ATT|ACA|CCA|GCT|AGA|CTA|GAT|GAA|TTA|TTA|TTC|TCA|GCT|ATC|TTA|GAA|AGC|153
|I|T|P|A|R|L|D|E|L|L|F|S|A|I|L|E|S|51
|CAC|GAT|GCT|AGA|AAA|GAA|CAC|AAA|CAA|TTC|GTA|GCA|GAA|TTA|AAA|GCA|AAC|204
|H|D|A|R|K|E|H|K|Q|F|V|A|E|L|K|A|N|68
|GAC|ATC|AAT|GTT|GTT|GAA|TTA|ATT|GAT|TTA|GTT|GCT|GAA|ACA|TAT|GAT|TTA|255
|D|I|N|V|V|E|L|I|D|L|V|A|E|T|Y|D|L|85
|GCA|TCA|CAA|GAA|GCT|AAA|GAT|AAA|TTA|ATC|GAA|GAA|TTT|TTA|GAA|GAC|TCA|306
|A|S|Q|E|A|K|D|K|L|I|E|E|F|L|E|D|S|102
|GAA|CCA|GTT|CTA|TCA|GAA|GAA|CAC|AAA|GTA|GTT|GTA|AGG|AAC|TTC|TTA|AAA|357
|E|P|V|L|S|E|E|H|K|V|V|V|R|N|F|L|K|119
|GCT|AAA|AAA|ACA|TCA|AGA|GAA|TTA|GTA|GAA|ATC|ATG|ATG|GCA|GGG|ATC|ACA|408
|A|K|K|T|S|R|E|L|V|E|I|M|M|A|G|I|T|136
|AAA|TAC|GAT|TTA|GGT|ATC|GAA|GCA|GAT|CAC|GAA|TTA|ATC|GTT|GAC|CCA|ATG|459
|K|Y|D|L|G|I|E|A|D|H|E|L|I|V|D|P|M|153
|CCA|AAC|CTA|TAC|TTC|ACA|CGT|GAC|CCA|TTT|GCA|TCA|GTA|GGT|AAT|GGT|GTA|510
|P|N|L|Y|F|T|R|D|P|F|A|S|V|G|N|G|V|170
|ACA|ATC|CAC|TAC|ATG|CGT|TAC|AAA|GTT|AGA|CAA|CGT|GAA|ACA|TTA|TTC|TCA|561
|T|I|H|Y|M|R|Y|K|V|R|Q|R|E|T|L|F|S|187
|AGA|TTT|GTA|TTC|TCA|AAT|CAC|CCT|AAA|CTA|ATT|AAC|ACA|CCA|TGG|TAC|TAC|612
|R|F|V|F|S|N|H|P|K|L|I|N|T|P|W|Y|Y|204
|GAC|CCT|TCA|CTA|AAA|TTA|TCA|ATC|GAA|GGT|GGA|GAC|GTA|TTT|ATC|TAC|AAC|663
|D|P|S|L|K|L|S|I|E|G|G|D|V|F|I|Y|N|221

FIG. 6 (continue)

```
AAT GAC ACA TTA GTA GTT GGT GTT TCT GAA AGA ACT GAC TTA CAA ACA GTT    714
 N   D   T   L   V   V   G   V   S   E   R   T   D   L   Q   T   V    238
ACT TTA TTA GCT AAA A(G)C ATT GTT GCT AAT AAA GAA TGT GAA TTC AAA CGT   765
 T   L   L   A   K  (S)  I   V   A   N   K   E   C   E   F   K   R    255
ATT GTT GCA ATT AAC GTT CCG AAA TGG ACA AAC TTA ATG CAC TTA GAC ACT    816
 I   V   A   I   N   V   P   K   W   T   N   L   M   H   L   D   T    272
TGG CTT ACT ATG TTA GAC AAG GAC AAA TTC CTA TAC TCA CCA ATC GCT AAC    867
 W   L   T   M   L   D   K   D   K   F   L   Y   S   P   I   A   N    299
GAC GTA TTT AAA TTT TGG GAT TAT GAC TTA GTA AAC GGT GGA GCA GAA CCA    918
 D   V   F   K   F   W   D   Y   D   L   V   N   G   A   E   P    316
CAA CCA GTT GAA AAC GGA TTA CCT CTA GAA GGA TTA TTA CAA TCA ATC ATT    969
 Q   P   V   E   N   G   L   P   L   E   G   L   L   Q   S   I   I    333
AAC AAA AAA CCA GTT (C)TA ATT CCT ATC GCA GGT GAA GGT GCT TCA CAA ATG  1020
 N   K   K   P   V   L   I   P   I   A   G   E   G   A   S   Q   M    350
GAA ATC GAA AGA GAA ACA CAC TTC GAT GGT ACA AAC TAC TTA GCA ATT AGA   1071
 E   I   E   R   E   T   H   F   D   G   T   N   Y   L   A   I   R    367
CCA GGT GTT GTA ATT GGT TAC TCA CGT AAC GAA AAA ACA AAC GCT GCT CTA   1122
 P   G   V   V   I   G   Y   S   R   N   E   K   T   N   A   A   L    384
GAA GCT GCA GGC ATT AAA GTT CTT CCA TTC CAC GGT AAC CAA TTA TCA TTA   1173
 E   A   A   G   I   K   V   L   P   F   H   G   N   Q   L   S   L    401
GGT ATG GGT AAC GCT CGT TGT ATG TCA ATG CCT TTA TCA CGT AAA GAT GTG   1224
 G   M   G   N   A   R   C   M   S   M   P   L   S   R   K   D   V    418
AAA TGG TAG                                                           1233
 K   W                                                                 420
```

\* nucleotide in circle : mutations in original clone,

\* nucleotide in box: site-directed mutation for codon usage in E.coli (a) Recombinant ADI overexpressed in BL21
(b) Finally purified recombinant ADI A: Bivine γ-globulin (Mr=158,000)
B: Chicken ovalbumin (Mr=44,000)
C: Equine myoglobin (Mr=17,000)
D: Vitamine B-12 (Mr=1,350)

PHARMACEUTICAL COMPOSITION COMPRISING ARGININE DEIMINASE FOR INHIBITING ANGIOGENESIS

FIELD OF THE INVENTION

The present invention relates to a pharmaceutical composition for inhibiting angiogenesis which comprises arginine deiminase as an active ingredient. More particularly, it pertains to a pharmaceutical composition comprising arginine deiminase or conjugates of the enzyme with activated polymers; said arginine deiminase can be obtained either by purification from *Mycoplasma arginini* or by a genetic recombination technique.

BACKGROUND OF THE INVENTION

Angiogenesis, the process of forming new capillary blood vessels from microvessels, occurs during embryonic development, wound healing and female menstruation, but not under normal conditions. A failure in angiogenesis regulatory system may lead to: angiogenesis-related diseases such as angioma, angiofibroma and blood vessel malformation; cardiovascular diseases such as arteriosclerosis, intravascular coagulation and edematous sclerosis; and ophthalmological diseases such as corneal transplantation-related neovasculogenesis, neovascular glaucoma, corneal disease, involutional macula, degeneration of macula, pterygium, retinal degeneration, retrolental fibroplasias and granular conjugativitis. In addition, such failure may result in chronic diseases such as rheumatism and dermatological diseases such as psoriasis, telangiectasis, pyogenic granuloma, seborrheic dermatitis and acne. Solid tumor growth and metastasis, in particular, are angiogenesis-dependent (*Ophthalmol.*, 102, 1261-1262, 1995; *J. Am. acad. Derm.*, 34(3), 486-497, 1996; *Circulation*, 93(4), 632-682, 1996; *Cell*, 86, 353-364, 1996).

Angiogenesis is accompanied by the processes of: degradation of the vascular basal membrane; migration and growth of the vascular endothelial cell; formation of canal cavity by differentiation of vascular endothelial cell; and reformation of the blood vessels. Normal angiogenesis occurs during the luteinization and placentation, but abnormal angiogenesis leads to such diseases as mentioned above. Therefore, there have been many attempts to develop compounds for the prevention and treatment of these angiogenesis-dependent diseases.

Arthritis, a well known inflammatory disease, is caused as an autoimmune disease. But if the abnormality continues to proceed, angiogenesis is induced by the chronic inflammation appearing in the synovial cavity in the joints and synovial cell. Then, the growth of vascular endothelial cell in the synovial cavity is induced by cytokine, which leads to the formation of articular lamina leak to eventually destroy such normal tissues as the cartilage which act as a cushion in the articulation (Koch A. E. et al., *Arthritis Rheum.*, 29, 471-479, 1986; Stupack D. G., *Braz. J. Med. Biol. Res.*, 32, 578-581, 1999; Koch A. E., *Arthritis Rheum.*, 41, 951-962, 1998).

Angiogenesis is one of major causes of ophthalmological disease, millions of people over the word are suffering from the loss of their eye power (Jeffrey M. I. and Takayuki A., *J. Clin. Invest.*, 103, 1231-1236, 1999). Such diseases as geriatric muscular degeneration, diabetic retinopathy, premature infant's retinopathy, neovascular glaucoma and corneal neovascularization are caused, at least partially, by angiogenesis (Adamin A. P., et al., *Angiogenesis*, 3, 9-14, 1999). Diabetic retinopathy, in particular, is a diabetic complication which leads to blindness through capillary vessel penetration into the vitrina.

The ocular tissue contains the least amount of blood vessels among all tissues, and abnormal blood vessel growth in the ocular tissue leads to blindness. Because there is no suitable treatment available for ophthalmological diseases caused by angiogenesis, only steroid or antibiotic treatment is practiced, together with cautery or photocoagulation at an advanced stage of the disease. However, these treatments are temporarily effective and the symptom recurs because of the failure to prevent angiogenesis. Therefore, an effective therapy for such diseases must be based on the inhibition of angiogenesis.

Psoriasis, represented especially by flush macula and scaly skin, is one of the proliferative disorders in the skin, and if not cured, it can cause pain and malformation. Normal horny cells usually divide once a month, but psoriatic skin cells, at least once a week. If the horny cell grows rapidly, angiogenesis takes place to supply blood (Folkman J., *J. Invest. Dermatol.*, 59, 40-48, 1972).

Angiogenesis is critical to the growth and metastasis of cancer cell. If angiogenesis is inhibited and the supply of blood is prevented, cancer cells grow to a size of about 1-2 mm in diameter and remain localized (Folkman and Tyler, Cancer Invasion and Metastasis; Biologic Mechanisms and Therapy [S. B. Day ed.], Raven press, New York, p 94-103, 1997).

Hitherto, there have been reported such angiogenesis inhibitors as the fumagillin and its derivative called AGM-1470 which inhibit the vascular endothelial cell growth, platelet factor-4 and its synthetic peptide, herbimycin A and the collagenase inhibitory tetracycline antibiotics.

Although arginine deiminase has been reported to inhibit the growth of cancerous cells in vivo and in vitro (Takalcu et al., *Int. J. Cancer*, 51, 244-249, 1992; Komada et al., *Int. J. Hematol.*, 65, 129-141, 1997; Misawa et al., *J. Biotechnol.*, 36, 145-155, 1994; Miyazaki et al., *Cancer Res.*, 50, 4522-4527, 1990; Sugimura et al., *Melanoma Res.*, 2, 191-196, 1992), it has not yet been disclosed as an angiogenesis inhibitor.

The bioavailibility of a protein drug is generally low because it is easily hydrolyzed and degraded by enzymes in vivo after it is administered, and if an immune response is induced by repeated administration thereof, life-threatening hypersensitivity may develop; furthermore, its clearance is enhanced by the reticuloendothelial system (RES).

U.S. Pat. No. 4,179,337 discloses a peptide-polymer complex prepared by linking a peptide or polypeptide to a polyethylene glycol (hereinafter, PEG) having a molecular weight of 500-20,000 or a water-soluble polymer. The in vivo biological activity of this complex remains high while the immune response against the complex is suppressed.

Abuchowski et al. have shown that the in vivo half-lives of various PEG-conjugated proteins are prolonged and their immunogenicities were low in the plasma (Abuchowski et al., *Cancer Biochem. Biophys.*, 7, 175-186, 1984), and Davis et al. have demonstrated that polyethylene glycol-uricase complex has an increased half-life and the side effect during the metabolism of uric acid is reduced (Davis et al., *Lancet.*, 2, 281-283, 1981). These results suggest that biologically active peptides or proteins, when conjugated to PEG, exhibit prolonged half-lives, increased solubilities and reduced immune responses.

Arginine deiminase has been known as an anti-cancer agent, but not as an inhibitor of angiogenesis. The present inventors have identified for the first time that arginine deiminase has inhibitory activity against angiogenesis. Arginine deiminase obtained from microorganisms or prepared by a genetic recombination technique, or said arginine deiminase conjugated to polymers like PEG, may have an extended in vivo half-life, reduced immunogenicity, and high activity of angiogenesis inhibition. The present inventors have thus found that arginine deiminase may be advantageously used in a pharmaceutical composition for inhibiting angiogenesis.

SUMMARY OF THE INVENTION

The primary object of the present invention is to provide a novel use of arginine deiminase having inhibitory activity against angiogenesis for preventing and/or treating various diseases related to angiogenesis.

BRIEF DESCRIPTION OF THE DRAWINGS

The above and other objects and features of the present invention will become apparent from the following description of the invention taken in conjunction with the following accompanying drawings; which respectively show:

FIGS. 1a to 1d show the effect of arginine deiminase treatment on the tube formation of HUVEC in Matrigel, wherein FIG. 1a represents, untreated, and FIG. 1b to 1d, treated with 10 μg/ml, 1 μg/ml and 0.4 μg/ml of arginine deiminase, respectively;

FIG. 6 illustrates the base sequence of arginine deiminase obtained in FIG. 5;

FIGS. 12a and 12b show the effect of PEG-arginine deiminase treatment on the tube formation of HUVEC on Matrigel, wherein FIG. 12a represents untreated, and 12b treated with 10 μg/ml of PEG-arginine deiminase respectively;

FIG. 13a shows the effect when treated with 1 μg/ml of PEG-arginine deiminase and FIG. 13b shows the effect when treated with PEG-arginine deiminase 1 μg/ml and arginine;

DETAILED DESCRIPTION OF THE INVENTION

Figure 1A:
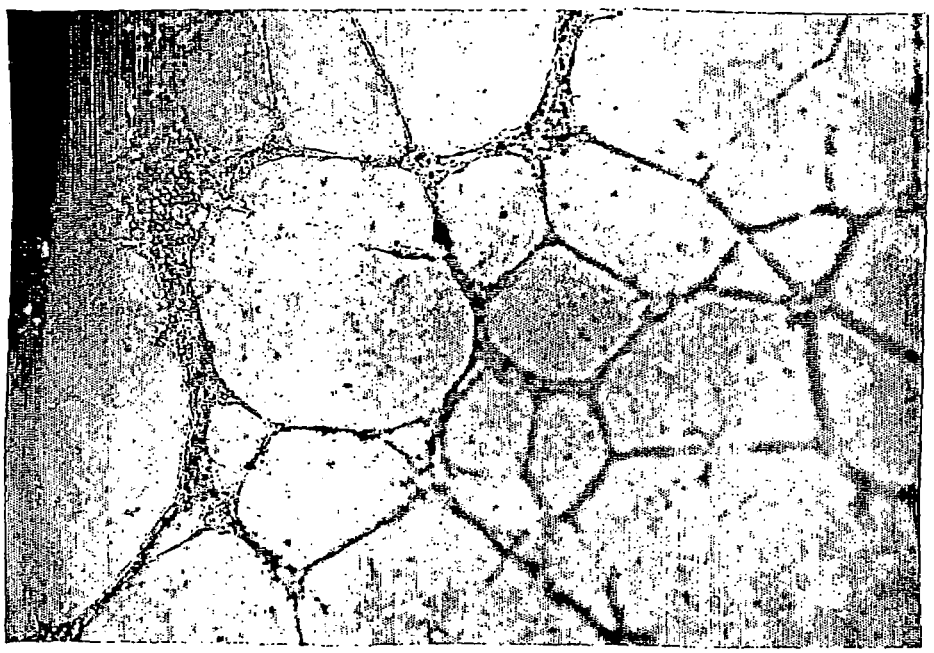

In accordance with the above object, the present invention provides a pharmaceutical composition comprising arginine deiminase as an active ingredient for inhibiting angiogenesis.

In the above-mentioned pharmaceutical composition, available arginine deiminase may be obtained from microorganisms such as *Mycoplasma* sp. or prepared by a genetic recombination method.

Further, pharmaceutical composition of the present invention may comprise complexes wherein arginine deiminase is conjugated with activated polymers such as PEG; the enzyme is either obtained from a microorganism or prepared by a genetic recombination method.

In order to provide arginine deiminase from a microorganism such as *Mycoplasma* sp., the present inventors isolated arginine deiminase from *Mycoplasma arginini* by conducting ion-exchange chromatography and affinity chromatography, and measured its activity.

Also, the present inventors isolate the genomic DNA from *Mycoplasma arginini*, conduct PCR, and clone the arginine deiminase gene to an expression vector plasmid. The tryptophan codon (TGA) specific to *Mycoplasma* sp. is replaced with TGG to overexpress arginine deiminase in *E. coli*. The arginine deiminase gene thus obtained is cloned to an *E. coli* overexpression vector, and an *E. coli* cell is transformed with this vector. The transformants are isolated, cultured in a large scale, and then, arginine deiminase is overexpressed for purification. Accordingly, the present invention provides the recombinant arginine deiminase protein encoded in the polynucleotide of SEQ ID No.: 9, or its equivalents and a derivative thereof.

In addition, arginine deiminase, purified or prepared by a genetic recombination method, is mixed with various activated polymers and the mixture is stirred to produce various polymer-ADI complexes.

In the present invention, one or more polymers selected from such water-soluble polymers as polyethylene glycol (PEG), polypropylene glycol (PPG), polyoxyethylene (POE), polytrimethylene glycol, polylactic acid and its derivative, polyacrylic acid and its derivative, polyphosphazenes, poly[L-lysine], polyalkylene oxide (PAO) and polysaccaride, and such nonimmune polymers as dextran, polyvinyl pyrrolidone, polyvinyl alcohol (PVA) and polyacryl amide may be used to offer a complex that has angiogenesis inhibitory activity, by conjugating thereto arginine deiminase, purified or prepared by genetic recombination method.

In the present invention, polymers having a molecular weight in the range of 200 to 100,000, preferably 1,000 to 45,000, may be used in the reaction.

The molar ratio of enzyme to activated polymer in the synthesis of the arginine deiminase-polymer complex of the present invention may range from 1:1 to 1:100, preferably from 1:1 to 1:50. The complexes linked one to 30 polymers to one enzyme molecule may be produced.

The conjugation reaction between enzyme and activated polymer may be carried out at a temperature ranging from 0 to 25° C. in 0.1 M phosphate buffer with pH 6 to 9 for a period of several minutes to 12 hours.

The activation of a polymer is conducted as follows; an unactivated polymer is converted into a polyalkylene oxide (PAO) form as monomethoxy-poly[ethylene glycol] (mPEG) and the other end-group of this PAO is converted into a reactive functional group to obtain an activated form of the polymer. The activated polymer is reacted with the ε-amine group in the lysine residue of the enzyme to form the enzyme-polymer complex. In addition to the amine group of the lysine, the carboxyl group, activated carbonyl group, oxidized sugar or mercapto group of the enzyme may be used as the conjugation site of the polymer.

The extent of the tube formation in the human vascular endothelial cells is measured to evaluate the inhibitory effect of arginine deiminase, purified or prepared by the recombination method as mentioned above, and the PEG-conjugated arginine deiminase. Also, the inhibitory effect of arginine deiminase on angiogenesis is determined by using the CAM assay and the mouse Matrigel model, two in vivo methods to measure the angiogenesis inhibitory effect.

Namely, human umbilical vein endothelial cells (HUVEC) are cultured on the gelified matrigel and then vascular formation, which is a process of angiogenesis, is induced. It is shown that the tube formation is strongly inhibited and the tube can not be formed when 10 µg/ml, 1 µg/ml or 0.4 µg/ml of arginine deiminase is added.

It is also confirmed that arginine deiminase inhibits angiogenesis in the CAM assay, an in vivo method to measure angiogenesis.

Therefore, the pharmaceutical composition comprising arginine deiminase as an active ingredient may be used as a drug for preventing and treating angiogenesis-dependent diseases.

The above-mentioned pharmaceutical composition is effectively used for treating not only arthritis, but also many angiogenesis-dependent ophthalmologic diseases, such as diabetic retinopathy, premature infant's retinopathy, neovascular glaucoma, involutional macula, degeneration of macula, pterygium, retinal degeneration, retrolental fibroplasias, granular conjugativitis and corneal disease. This composition is also useful for preventing and/or treating angioma, angiofibroma, and some dermatologic diseases such as psoriasis, telangiectasis, pyogenic granuloma, seborrheic dermatitis and acne, and cancer metastasis.

As mentioned above, arginine deiminase, isolated from a microorganism or obtained by genetic recombination method, and a complex thereof conjugated to an activated polymer may be mixed with general carriers. In order to prepare oral formulations such as tablets, capsules, pills, granules, suspensions and solutions, the formulations for injection such as solutions or suspensions, or dried powders that may be mixed with distilled water before injection, the locally-applicable formulations such as ointments, creams and lotions, and other formulations in accordance with any of the conventional procedures in the pharmaceutical field.

Carriers generally used in the pharmaceutical field may be employed in the composition of the present invention. For example, orally-administered formulations may include binders, emulsifiers, disintegrating agents, excipients, solubilizing agents, dispersing agents, stabilizing agents, suspending agents, coloring agents or spicery. Injection formulations may comprise preservatives, unagonizing agents, solubilizing agents or stabilizing agents. Preparation for local administration may contain bases, excipients, lubricants or preservatives. Any of the suitable formulations known in the art (Remington's Pharmaceutical Science [the new edition], Mack Publishing Company, Eaton Pa.) may be used in the present invention.

The inventive pharmaceutical composition can be clinically administered as various oral and parenteral formulations A suitable formulation may be prepared using such excipients as additives, enhancers, binders, wetting agents, disintegrating agents and surfactants, or diluents. Solid formulations for oral administration include pills, tablets, dusting powder, granules and capsules. Those solid formulations may be prepared by mixing one or more excipients, e.g., starch, calcium carbonate, sucrose, lactose and gelatin with dibenzylbuthyllacton lignan derivatives. Also, lubricants such as magnesium stearate and talc may be included in the present formulation. Liquid formulations for oral administration include suspension, solution, emulsion and syrup. Those formulations may contain wetting agents, sweeteners, aromatics and preservatives, in addition to general simple diluents such as water and liquid paraffin. Formulations for parenteral administration include sterilized aqueous solution, suspension, emulsions freeze-dried alternative treatment and suppositories. Water-insoluble excipients and suspending agents comprise vegetable fats such as propylene glycol, polyethylene glycol and olive oil, and injectable esters such as ethyl oleate. Witepsol®, Macrogol, ®Tween® 61, cacao fats, laurin fats and glycerogelatins may be used as bases of suppositories.

The pharmaceutical composition may be administered orally or via parenteral routes such as intravenous, intramuscular, subcutaneous, intraabdominal, sternal and arterial injection or infusion, or topically through rectal, intranasal, inhalational or intraocular administration.

The typical daily dose of arginine deiminase of the present invention may range from 0.05 to 200 mg/kg body weight, preferably from 0.1 to 100 mg/kg body weight and can be administrated in a single dose or in divided dose. However, it should be understood that the amount of the active ingredient actually administered ought to be determined in light of various relevant factors including the conditions to be treated, the chosen route of administration, the age, sex and body weight of the individual patient, and the severity of the patient's symptom. Therefore, the above dose should not be construed as a limitation to the scope of the invention in any way.

The following examples are intended to further illustrate the present invention without limiting its scope.

EXAMPLE 1

Purification of Arginine Deiminase

*Mycoplasma arginini* was inoculated and cultured in PPLO broth containing 20% horse serum, 2.5% yeast extract and 1% L-arginine to obtain arginine deiminase therefrom.

The culture was centrifuged at 15,000 g for 20 minutes and the precipitated cells were washed twice with 30 ml of the 10 mM potassium phosphate, pH 7.0. The resulting cell precipitates were suspended in 10 ml of 10 mM potassium phosphate buffer, pH 7.0, sonicated at 20 kHz in an ice bath for 15 minutes, and centrifuged to collect the supernatant. The resulting supernatant was subjected to the following purification steps carried out in a cold chamber maintained at 4° C.

First, the cell lysate was passed through a DEAE anion exchange column (Amersham Pharmacia, Cat. No.: 17-0709) pre-equilibrated with 10 mM potassium phosphate buffer, pH 7.0. The column was then washed with a sufficient amount of buffer (three times column volume) to minimize the non-specific binding, and fractionated under a 0-1 M NaCl salt gradient. The arginine deiminase activity of each fraction was measured to identify active fractions.

The active fractions were pooled and precipitated with 0-80% ammonium sulfate to obtain pellets. The pellets were dissolved in 1 M ammonium sulfate, passed through a phenyl sepharose column (Amersham Pharmacia, Cat. No.: 17-0965) pre-equilibrated with 1 M ammonium sulfate, and fractionated under a reverse-phase salt gradient of 1-0 M ammonium sulfate. The activity of each fraction was measured, active fractions were combined and dialysed for 14 hours in 10 mM potassium phosphate buffer.

The resulting dialysate was passed through an arginine-sepharose affinity column (Amersham Pharmacia, Cat. No.: 17-0524) pre-equilibrated with 10 mM potassium phosphate buffer, washed with the same buffer, and subjected to a salt gradient of 0-1.5 M NaCl. The activity of each fraction was measured and the fractions containing pure arginine deiminase were combined, concentrated and desalted by using an ultrafiltration unit (YM10).

EXAMPLE 2

Measurement of Arginine Deiminase Activity

Arginine deiminase obtained from *Mycoplasma arginini* is an enzyme having activity to remove the imine group from arginine to produce citrulline. The activity of arginine deiminase may thus be estimated by measuring the citrulline level produced in the reaction mixture.

The level of the citrulline produced from arginine deiminase was measured by the calorimetric determination described by Boyde and Rahmatulah (Boyde T. R. and Rahmatulah M., *Anal. Biochem.*, 107, 424-431, 1980). An aliquot (0.1 ml) of the enzyme solution and 10 mM L-arginine were added to 1 ml of 0.1 M potassium phosphate buffer, pH 7.0 and the resulting solution was incubated at 37° C. for 5 minutes. After the reaction was complete, the reaction mixture was deproteinized with 5% TCA solution and centrifuged.

A 0.1 ml portion of the supernatant was transferred to a new tube, 2 ml of a ferric acid solution (550 ml of deionized water, 200 ml of concentrated phosphoric acid, 250 ml of sulfuric acid and 150 ml of ferric chloride) and 1 ml of a diacetyl monoxime solution (5 mg of thiosemicarbazide, 50 ml of deionized water and 250 nm of diacetyl monoxime) were added thereto. The mixture was heated in a boiling water bath for 5 minutes, cooled to room temperature, and the optical density at 530 nm was measured. 1 mM citrulline was diluted and used as a standard solution.

A total 7 mg of protein was obtained from 600 mg of *Mycoplasma arginini* and 250 µg of pure arginine deiminase was recovered therefrom by way of conducting chromatography using DEAE-sepharose, phenyl-sepharose and arginine-sepharose columns. Defining one unit as the amount of the enzyme needed to convert 1 µmole of arginine into citrulline at 37° C. in 1 minute, the specific activity of the purified arginine deiminase was found to be 31.36 units/mg of the protein. The conversion reaction was carried out in 0.1 M potassium phosphate buffer, pH 7.4 with 10 mM L-arginine.

EXAMPLE 3

Production of Recombinant Arginine Deiminase (3-1) Substitution of the Codon Usage of the Arginine Deiminase Gene The genomic DNA was isolated from *Mycoplasma arginini*, ATCC 23243 and subjected to a polymerase chain reaction (PCR) using primers specific to arginine deiminase gene, and the PCR product was cloned to pBluescript KS(+).

In *Mycoplasma arginini*, the TGA stop codon is specifically recognized as tryptophan (Misawa et al., *J. Biotechnol.*, 36, 145-155, 1994), and this TGA codon was replaced with TGG tryptophan codon in order to overexpress the arginine deiminase gene in *E. coli*.

The arginine deiminase gene has a total of 5 TGA codons. The last TGA codon was previously mutated by inserting TGG codon in the 3'-primer during the first PCR. The remaining four TGA codons were substituted by site-directed mutagenesis during the process of overlap extension by PCR with the antisense and sense oligonucleotides of SEQ ID No's.: 1 to 8, respectively, described by Steffan et al. (*Vet. Parasitol.*, 31, 269-273, 1989). The resulting product was cloned to the pBluescrip KS(+) and the DNA sequencing was carried out to confirm the sequence of the mutated sites (FIG. 6, SEQ ID No.: 9).

(3-2) Overexpression and Purification in *E. coli*

Figure 5:
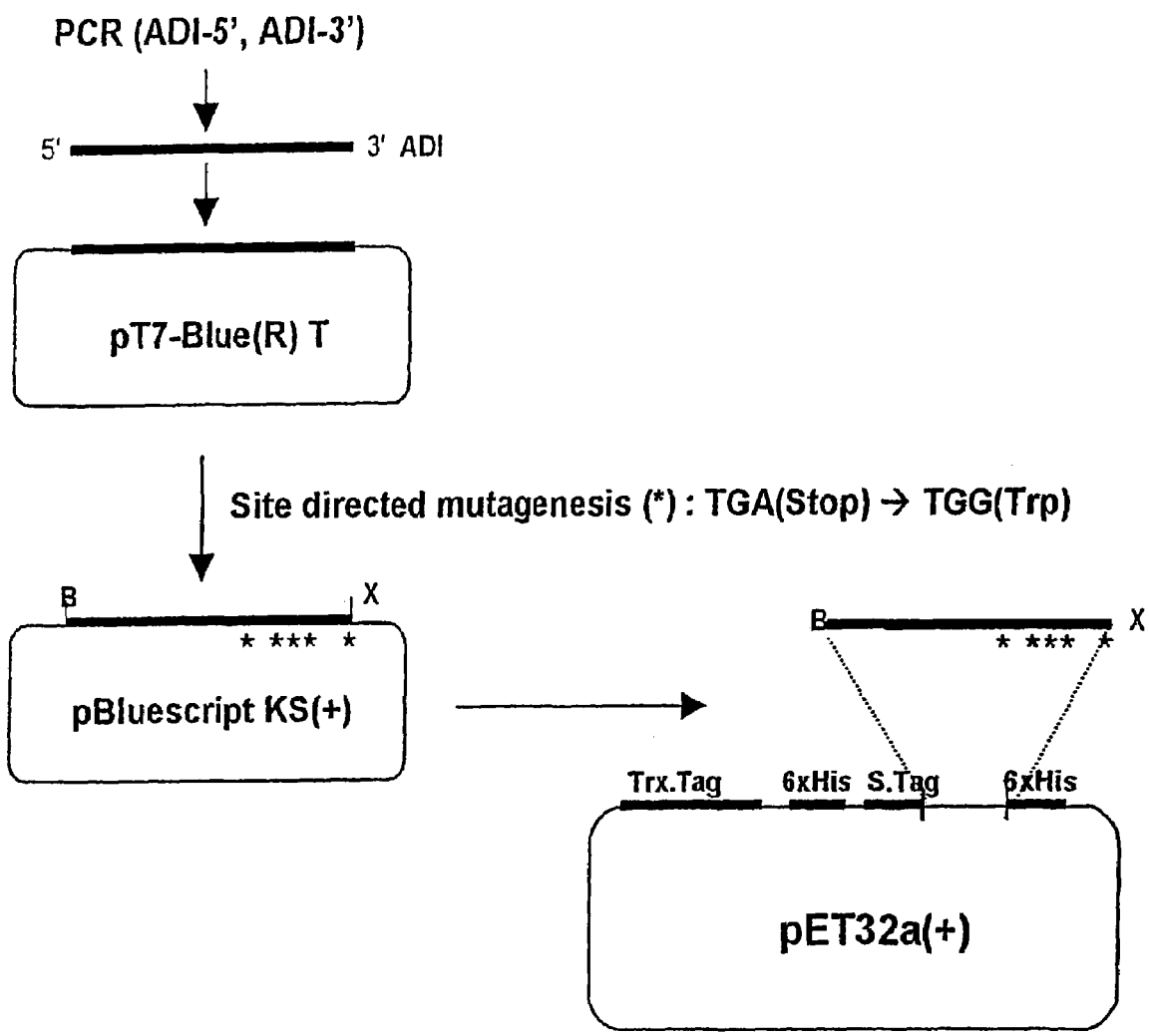
FIG. 5 describes the PCR-directed mutagenesis procedure of arginine deiminase from *Mycoplasma arginini*.
Figure 7:
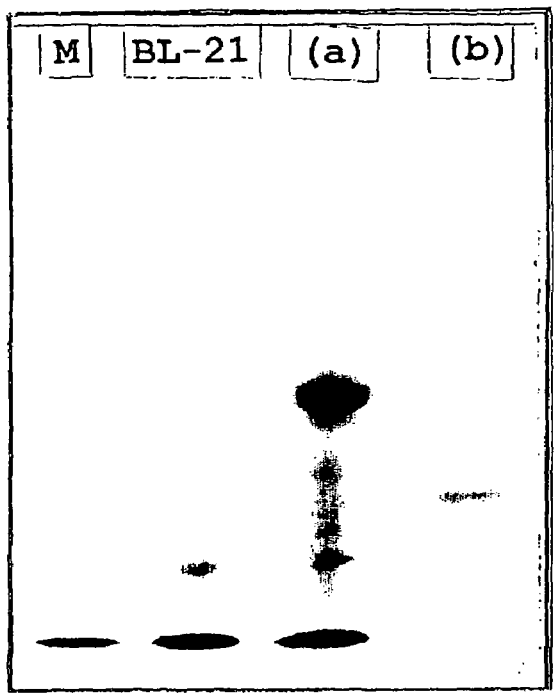
FIG. 7 demonstrates the SDS-PAGE analysis to measure the molecular weight of the overexpressed recombinant thioredoxin-linked arginine deiminase (67 kDa) and the purified arginine deiminase (45 kDa)

To overexpress the above recombinant arginine deiminase (designated ADI) gene in *E. coli*, the ADI gene was cloned to the BamH I and Xho I sites of pET-32a expression vector (Novagen, USA) to construct pET32a/ADI (FIG. 5). Plasmid pET32a/ADI was transformed into *E. coli* BL-21, and the transformed *E. coli* was isolated and then cultured in a large scale. The recombinant ADI was overexpressed by induction with 1 mM of IPTG, and analyzed by SDS-PAGE showing that the molecular weight of ADI was about 63 kDa (Lane (a) of FIG. 7). Almost all of the recombinant ADI were overexpressed in the form of an inclusion body. The inclusion bodies were collected, denatured in a guanidine-HCl solution and neutralized for 48 hours.

The neutralized ADI solution was subjected to ion-exchange and affinity chromatographies according to the method by Kang et al. (Kang et al., *Mol. Cells*, 10, 343-347, 2000), and active fractions were collected. When the collected fractions were analyzed by SDS-PAGE, it was found that the combined active fractions contained pure ADI protein of about 45 kDa (Lane (b) in FIG. 7), which was somewhat different from the molecular weight of the initially overexpressed ADI in *E. coli*.

Figure 8:
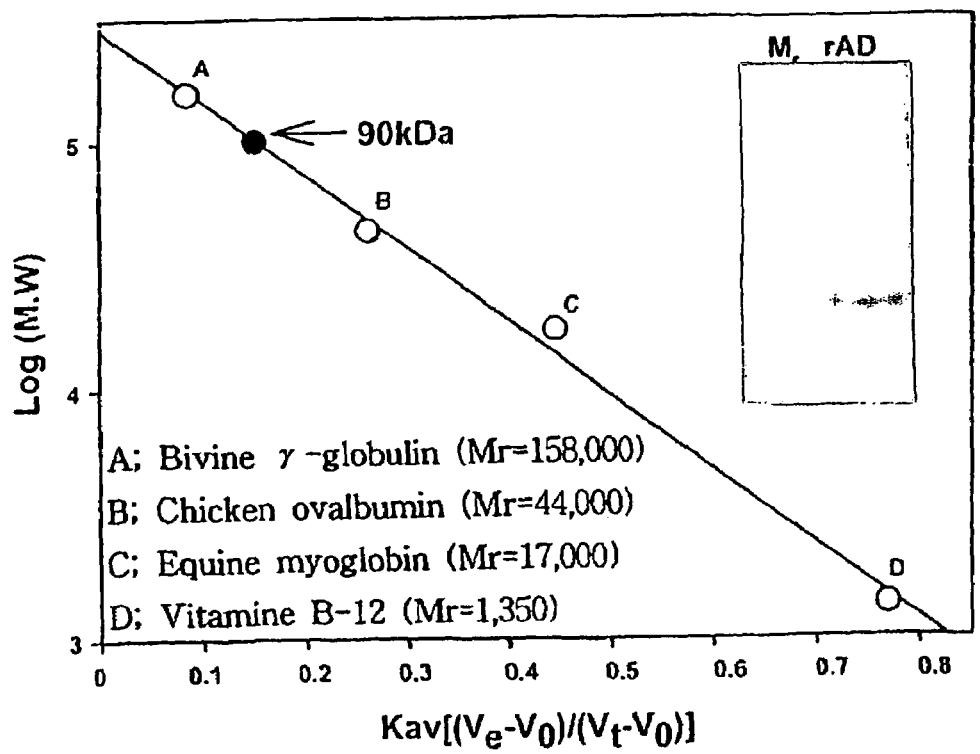
FIG. 8 shows the native-PAGE analysis to confirm the dimer (90 kDa) of arginine deiminase.

The analysis of the N-terminal amino acid sequence of the purified ADI showed that a portion of the amino acid sequence in the S-Tag from the pET-32a was self-processed. The native-PAGE and sephacryl S-100 column (Amersham Pharmacia, Cat. No. 17-0612-01) chromatographic analyses also confirmed that ADI exists as a dimer having a molecular weight of 90 kDa (FIG. 8).

(3-3) Activity and Stability of the Recombinant ADI

Figure 9:
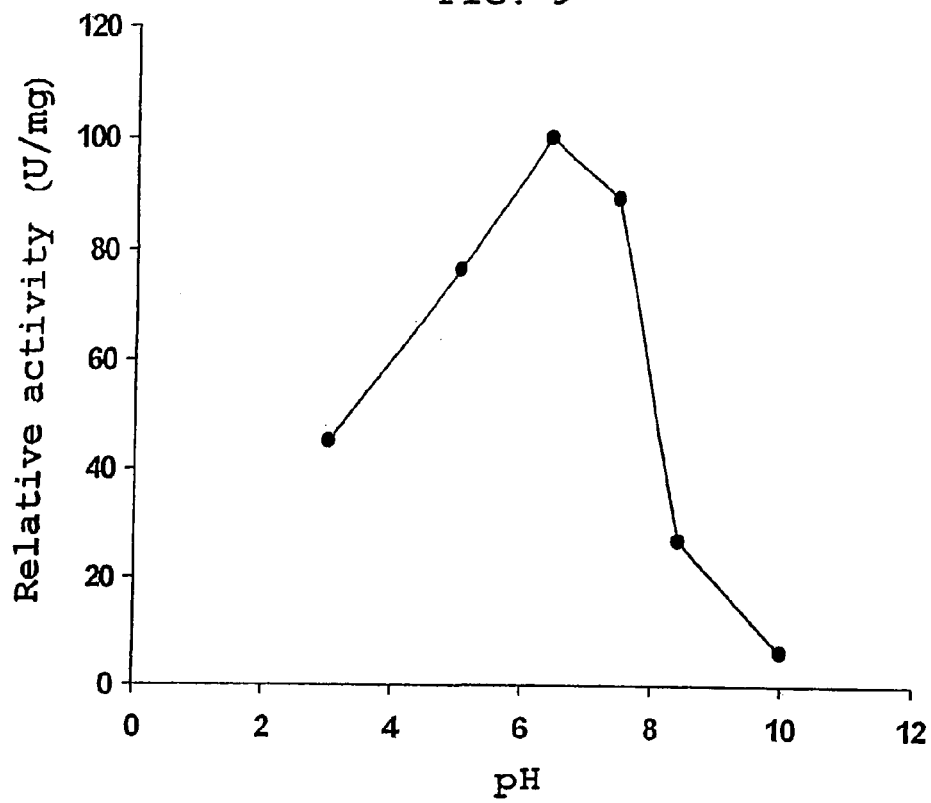
FIG. 9 displays the variation in activity of recombinant arginine deiminase with changing the pH.
Figure 10:
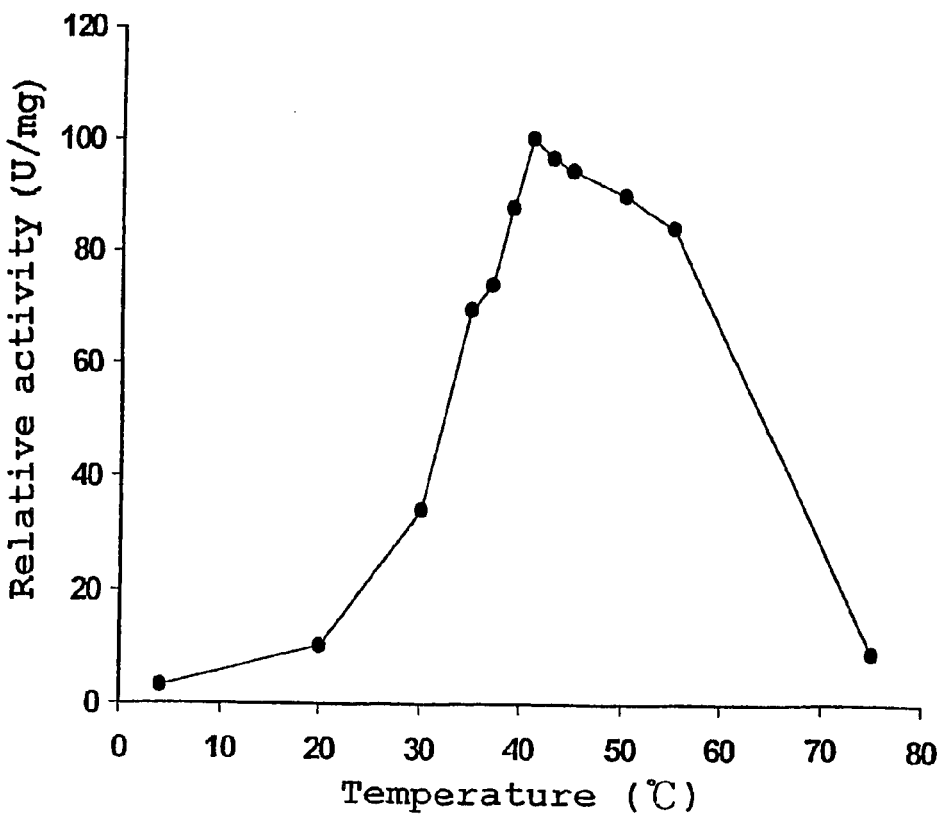
FIG. 10 shows the variation in activity of recombinant arginine deiminase with changing temperature.
Figure 11:
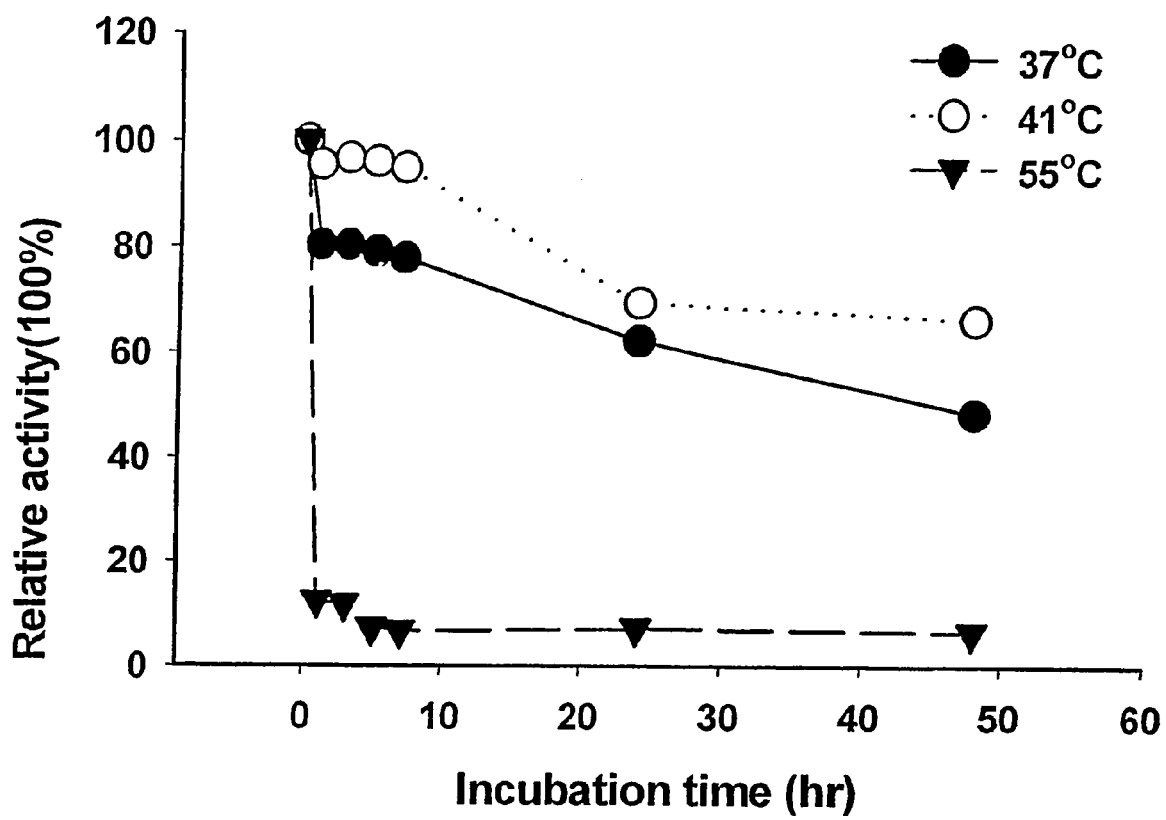
FIG. 11 shows the activity of recombinant arginine deiminase at 41° C. with changing incubation time.

The method of determining the amount of citrulline produced from arginine was applied to measure the activity of recombinant ADI (Boyde et al., *Anal. Biochem.*, 107, 424-431, 1980). The recombinant ADI had similar activity as the ADI purified from *Mycoplasma arginini*, and optimal temperature was 41° C. in 20 mM potassium phosphate buffer solution, pH7.4 (FIG. 9) and optimal pH was 6.4 (FIG. 10). Also, it remains stable with 70% of its original activity for 48 hours at 41° C. and pH 7.4 (FIG. 11).

EXAMPLE 4

Effect of ADI on the Tube Formation of the HUVEC Cell on the Matrigel

To examine the effect of ADI on angiogenesis in an in vitro experiment, capillary vessel formation in the human vascular endothelial cells was studied. First, human umbilical vein endothelial cell (HUVEC) was isolated to carry out the tube formation experiment.

Figure 2:
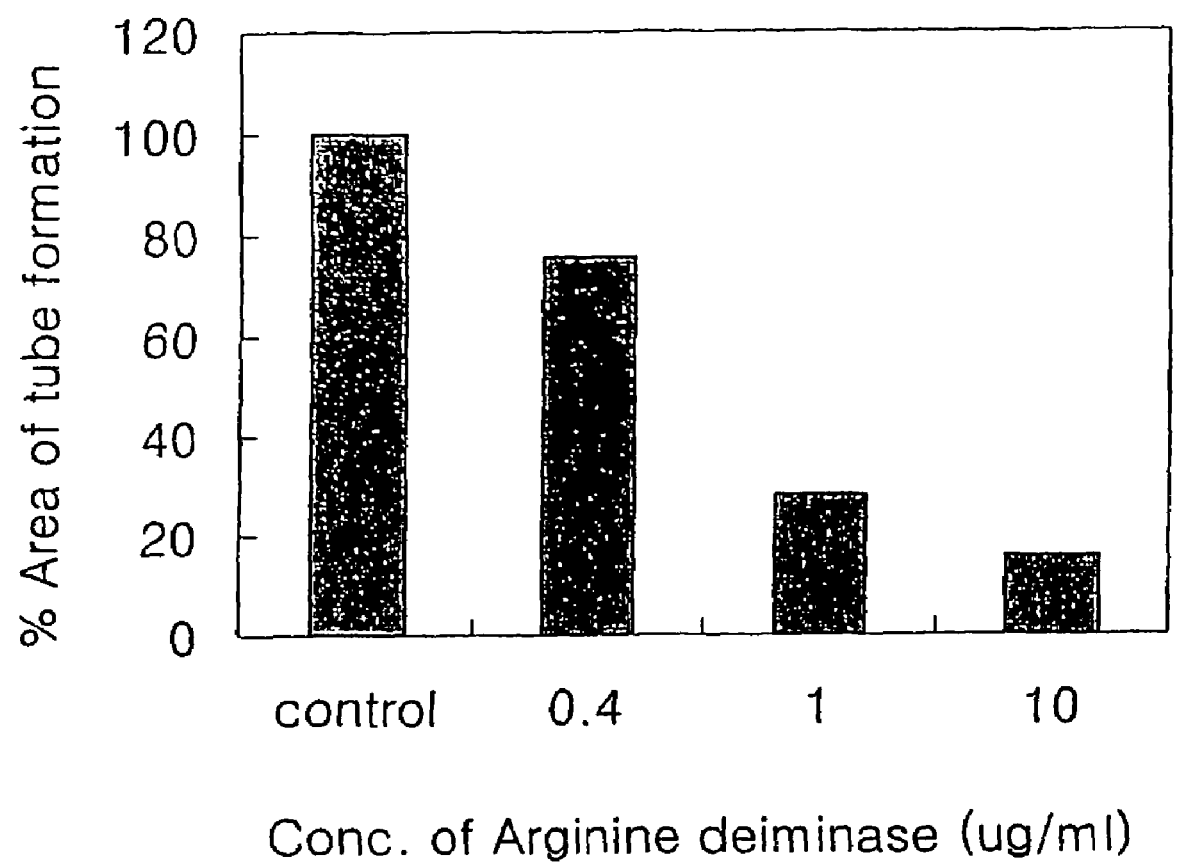
FIG. 2 provides a graph showing the inhibiting effect of arginine deiminase on tube formation of HUVEC.

Endothelial cells of the vein were isolated from fresh human cords obtained during Caesarean operation and cultured on Matrigel. It was confirmed by immunocytochemical staining with the antibody against VIII factor that HUVEC had been successfully isolated. The resulting vascular endothelial cells were cultured on Matrigel (Matrigel, B D Bioscience, USA, Cat. No. 354234). The endothelial cells formed two-dimensional tubes on gelified Matrigel. The reticular tube structure were shown when the endothelial cells were cultured at 37° C. for 16-18 hours, and it may be considered as one of steps in angiogenesis. The effects of ADI on angiogenesis were observed when treated with 10 μg/ml, 1 μg/ml and 0.4 μg/ml of ADI. ADI of this experiment was purified from *Mycoplasma arginini*, and the results are shown in FIG. 2 and Table I.

TABLE I

| Concentration of ADI | Area of Tube (%) |
|---|---|
| Control | 100 |
| 0.4 μg/ml | 75.7 |
| 1 μg/ml | 28.1 |
| 10 μg/ml | 15.8 |

Figure 1B:
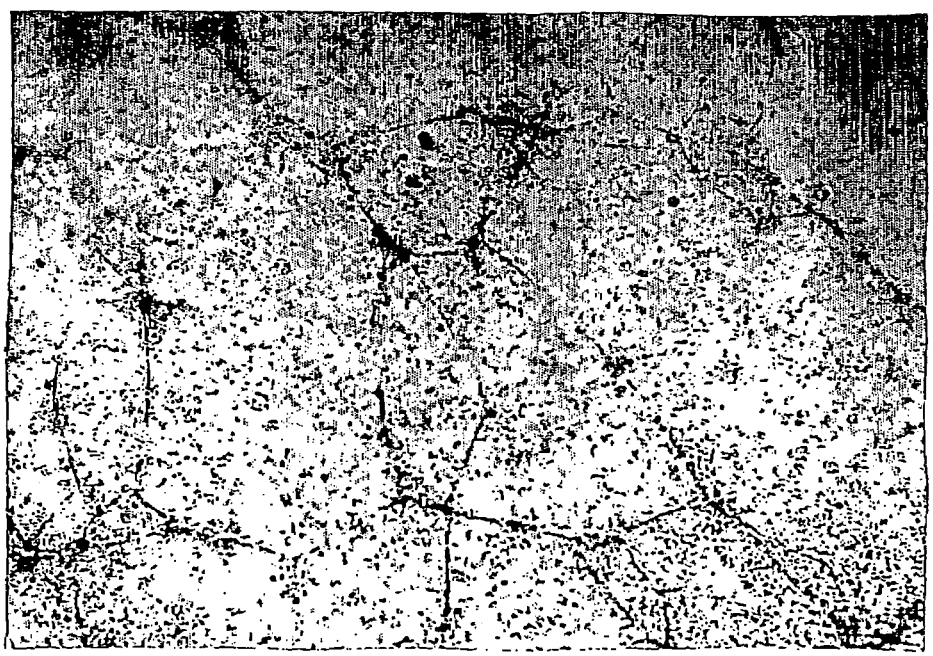
Figure 1C:
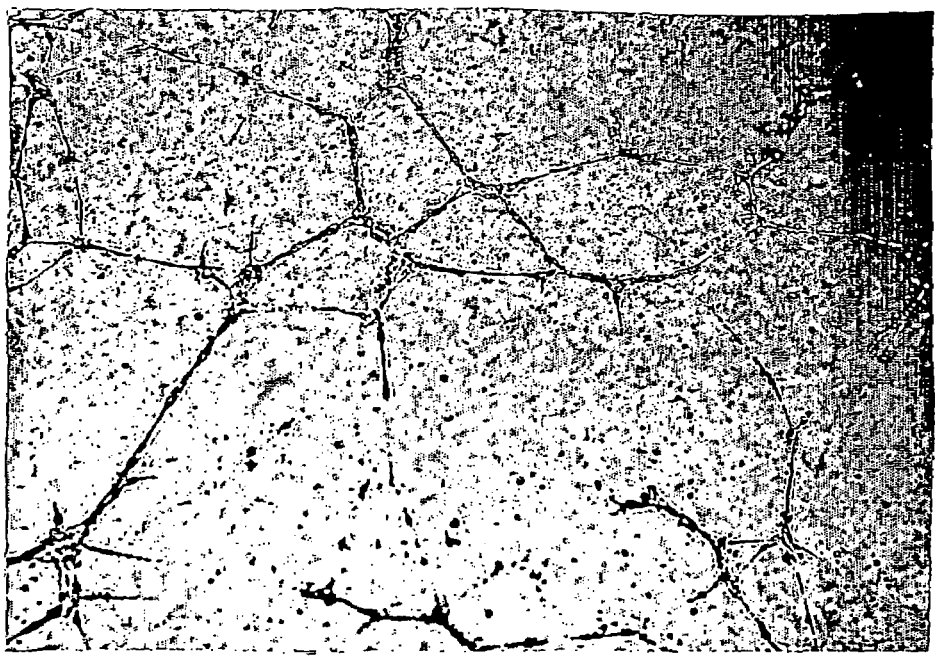
Figure 1D:
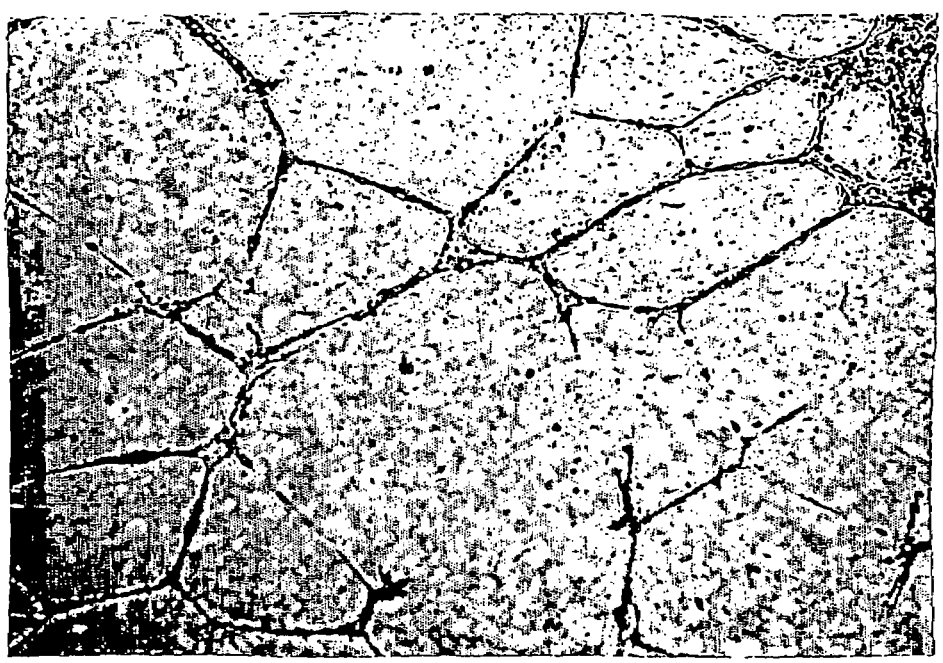

As the result shows, the tube formation was strongly inhibited by 10 μg/ml of ADI and the tube-forming cells were not properly shaped (FIG. 1b). When treated with 1 μg/ml or 0.4 μg/ml of ADI, the tube formation was suppressed as compared with the control (FIG. 1a), and exhibited disconnections in the tube (FIG. 1c and FIG. 1d). The tube formation was inhibited, relative to the control group, in a concentration-dependent manner. The area of tube formation in Table I was determined by using image analysis program Image-Pro Plus (Media Cybernetica, USA).

EXAMPLE 5

CAM Assay to Measure Angiogenesis

Fertilized chicken eggs were incubated for three days in an incubator maintained at a relative humidity of over 70% at 37° C. From each egg, 2-3 ml of albumin was extracted using a 26 gauge syringe and the egg was sealed with a transparent adhesive tape to prevent drying, and then, a window of 1×1 cm size was made in the central region of the fertilized egg by drilling. 1 μg of recombinant ADI obtained in Example 3 was solubilized in 10 μg of distilled water, the resulting solution was dried on Thermanox disc (Miles Scientific co.), and laid on the chorioallantoic membrane of the egg exposed through the window. The egg was then sealed with a transparent adhesive tape and incubated for 3 days in the incubator.

To distinguish the blood vessels in the allantoic cavity from those distributed in the chorioallantoic membrane, Intralipid was injected into the allantoic cavity with a 26 gauge syringe to shield the blood vessels in the allantoic cavity, and the change of the blood vessels in the chorioallantoic membrane was observed.

Figure 3:
FIG. 3 presents a photograph showing angiogenesis inhibition by arginine deiminase in the Chorioallantoic membrane (CAM) assay.
Figure 4:
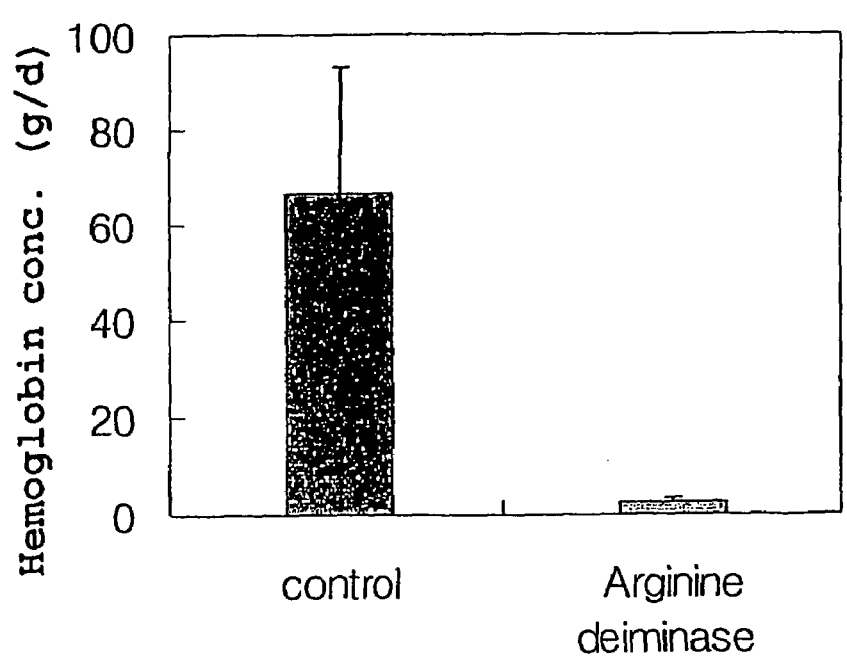
FIG. 4 shows the result of measuring angiogenesis inhibition by arginine deiminase in the mouse Matrigel model.

As shown in, FIG. 3, angiogenesis in the chorioallantoic membrane of the fertilized control egg was not affected but the formation of the capillary vessels was significantly inhibited by 1 μg of ADI and angiogenesis was inhibited to the extent of 88% when the fertilized egg was treated with 1 μg of ADI.

EXAMPLE 6

Animal Experiment to Measure Angiogenesis (a Mouse Matrigel Model)

The inhibitory effect of ADI on angiogenesis was measured using in vivo mouse Matrigel model. In order to induce angiogenesis, a mixture of 0.4 ml of Matrigel (Collaborative Biomedical Products), 50 ng/ml of basic fibroblast growth factor (FGF) and 50 units/ml of heparin were injected subcutaneously to each 6-8 week-old C57BL/6 mouse (control group). For each mouse in the ADI-treated group, 8.9 μg/head of recombinant ADI obtained in Example 3 was included in the Matrigel.

After 3-5 days, the epidermis was removed, Matrigel was carefully recovered and the hemoglobin content was measured with the Drabkin reagent (Sigma). As shown in Table II, angiogenesis was almost completely inhibited in the ADI-treated experimental group, as compared with the control group.

TABLE II

| | Content of Hemoglobin (g/dl) |
|---|---|
| Control group | 66.4 ± 27.6 |
| ADI-treated group | 2.5 ± 0.1 |

EXAMPLE 7

Production of PEG5000-ADI

Monomethoxy-poly (ethylene glycol) was made from PEG 5000 (Shearwater Corp. Huntsville, Ala., USA) according to the method described by Abuchowski et al. (*Cancer Biochem. Biophys.*, 7, 175-186, 1984), to protect one terminal hydroxyl group of PEG, and treated with phosgene and N-hydroxysuccinimide to obtain ester of succinyl-N-hydroxysuccinimide monomethoxy-poly (ethylene glycol) (designated SS-PEG). Activated SS-PEG (2 mg) solubilized in 0.1 M phosphate buffer, pH 8.0 was added to 0.2 mg of 5 mg/ml ADI purified from *Mycoplasma arginini* or prepared by the genetic recombination method in 0.1 M phosphate buffer, pH 8.0. The mixture was shaken for 30 minutes at room temperature, and 0.1 M glycine was included in the reaction mixture to stop the reaction. PEG5000-ADI was recovered after removal of unreacted ADI and PEG by dialysis in phosphate buffered saline (PBS), pH 7.4.

EXAMPLE 8

Production of Branched PEG25000-ADI

Branched PEG2-COOH (MW 5,000) (Shearwater Corp., Huntsville, Ala., USA) was activated with succinimidyl succinate, and 5 mg of the activated branched SS-PEG25000 was used to make branched PEG25000-ADI, according to the procedure of Example 7.

EXAMPLE 9

Production of PEG220000-ADI

Branched PEG2-COOH (MW 20,000) (Shearwater Corp., Huntsville, Ala., USA) was activated with succinimidyl succinate, and 10 mg of the activated branched PEG220000 was used to make branched PEG220000-ADI, according to the procedure of Example 7.

EXAMPLE 10

Production of PEG-ADI at Various pH 6.8 μl of ADI (10 mg/ml) and 10 μl of SS-PEG5000 (10 mg/ml) were mixed in 0.1 M phosphate buffer having a pH in the range of 5 to 9, and then the mixture was shaken at room temperature for 30 minutes. The reaction was stopped with 5 μl of 1 M glycine. Unreacted ADI and PEG were removed by dialysis in PBS at pH 7.4 to obtain PEG-ADI.

EXAMPLE 11

Production of PEG-ADI Using Various Molar Ratio of SS-PEG/ADI

Using 10 μl of SS-PEG solution and 6.8 μl of ADI (10 mg/ml), 4 mixtures having ADI: SS-PEG molar ratio of 1:10, 1:20, 1:50 and 1:100 were prepared and subjected to the procedure of Example 7.

EXAMPLE 12

Measurement of PEG-ADI Enzyme Activity

The enzyme activities of PEG-ADIs produced in Examples 7 to 11 were measured by the method of Example 3. The result showed that all the PEG-ADI conjugates had an activity of over 80% based on that of unconjugated ADI.

EXAMPLE 13

Effect of PEG-ADI on the Tube Formation in HUVEC

Figure 12A:
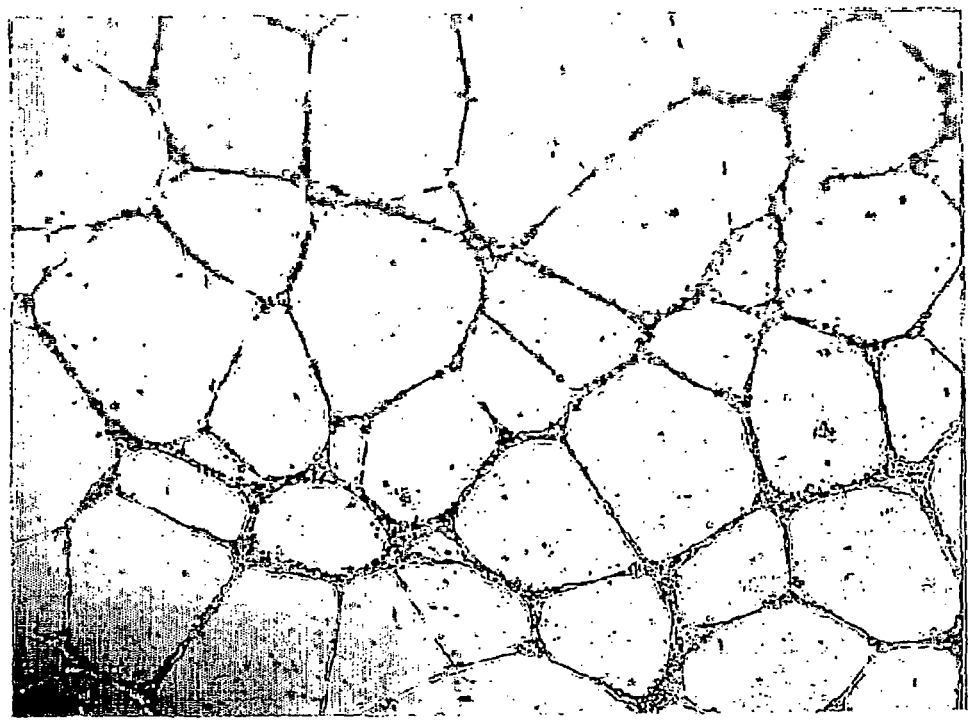
Figure 12B:
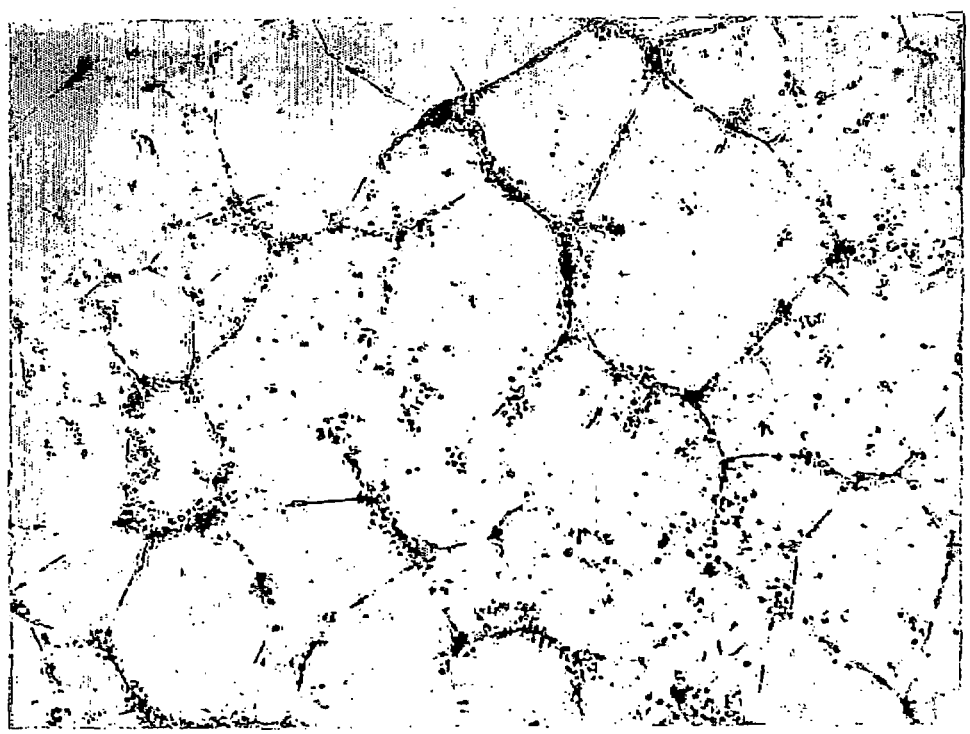
Figure 13A:
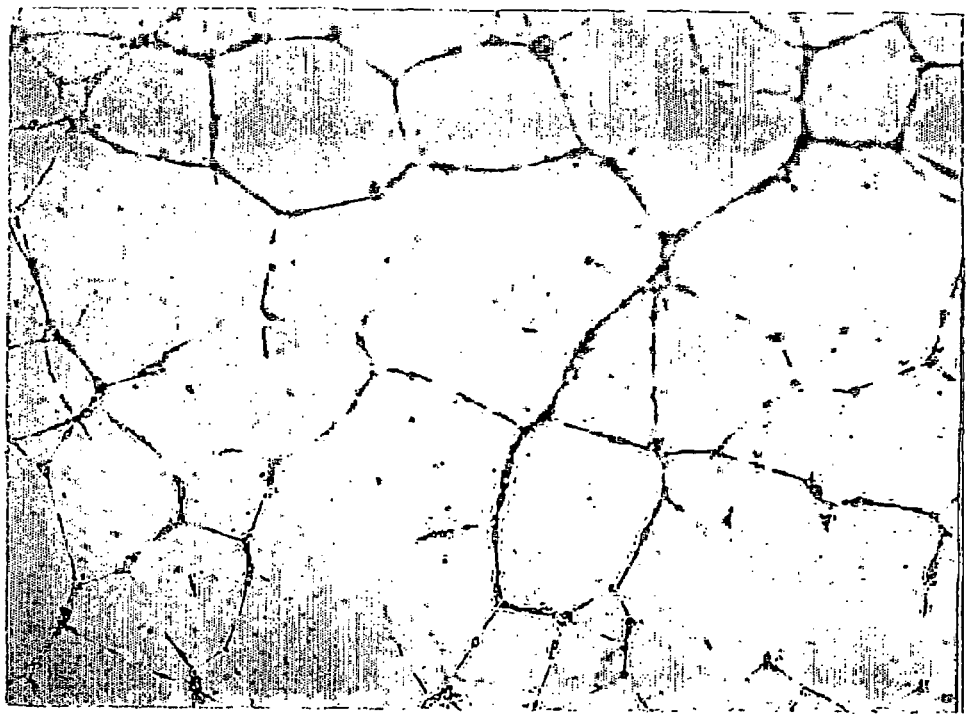
FIGS. 13a and 13b show the inhibitory mechanism of PEG-arginine deiminase in the HUVEC tube formation.
Figure 13B:
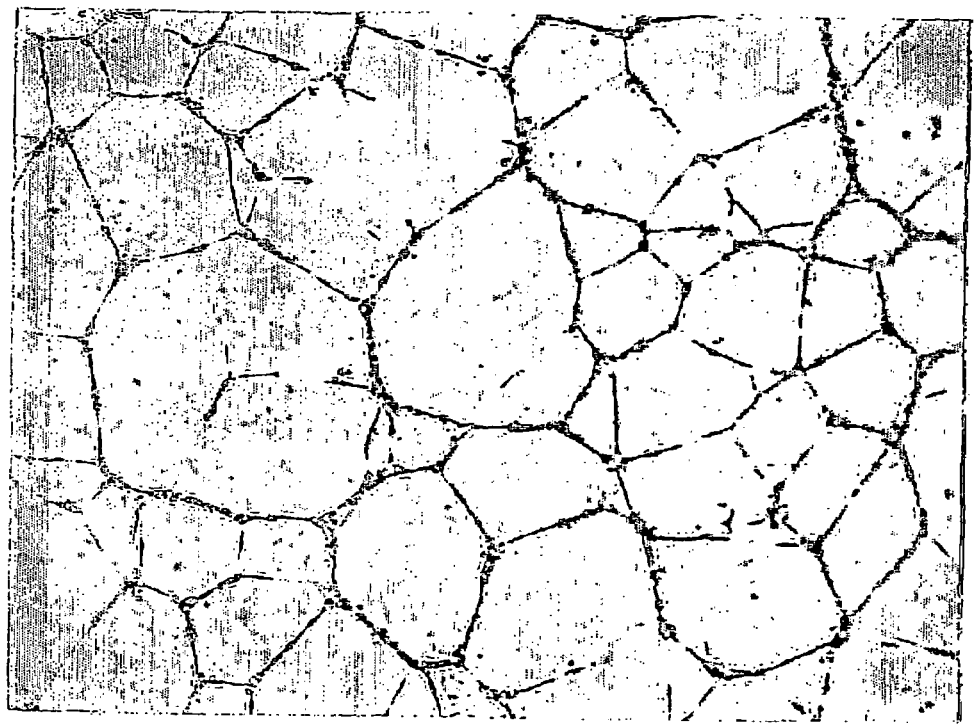

To examine the anti-angiogenic activity of PEG-ADI, an experiment was conducted using PEG5000-ADI as a representative PEG-ADI. Human HUVEC was treated with 10 μg/ml or 1 μg/ml of PEG-ADI and cultured on gelified Matrigel at 37° C. for 16-18 hours to observe its effect on the reticular tube formation of the endothelial cells. The result showed that the tube formation was strongly inhibited by 10 μg/ml of PEG-ADI and the tube-forming cells were deformed as compared with the control (FIGS. 12a and 12b), and the tube formation was also strongly suppressed by adding 1 μg/ml of PEG-ADI. In order to see whether the inhibition of tube formation by PEG-ADI is due to the depletion of the arginine as a NO donor, 2 mM of arginine was added in a repeat run with 1 μg/ml of PEG-ADI (FIGS. 13a and 13b). The inhibitory effect of PEG-ADI on tube formation in this run was reversed in the presence of arginine (FIG. 13b): the extent of the formed tube was similar to that of the control group. Accordingly, it was confirmed that PEG-ADI inhibited the tube formation by depleting the arginine in the cell.

EXAMPLE 14

The CAM Assay of PEG-ADI

The chorioallantoic membrane (CAM) assay of Example 5 was repeated to measure the in vivo inhibitory effect of PEG-ADI on angiogenesis.

Figure 14:
FIG. 14 is the result of the CAM assay showing the inhibitory effect of PEG-arginine deiminase on angiogenesis.

The result showed that there was no change in the capillary blood vessels in saline-treated fertilized eggs, while angiogenesis inhibition was observed in 81% (n=16) of PEG-ADI-treated fertilized eggs (FIG. 14).

EXAMPLE 15

The Inhibitory Effect of PEG-ADI on Angiogenesis in Animal Experiment (a Mouse Matrigel Model)

Figure 15:
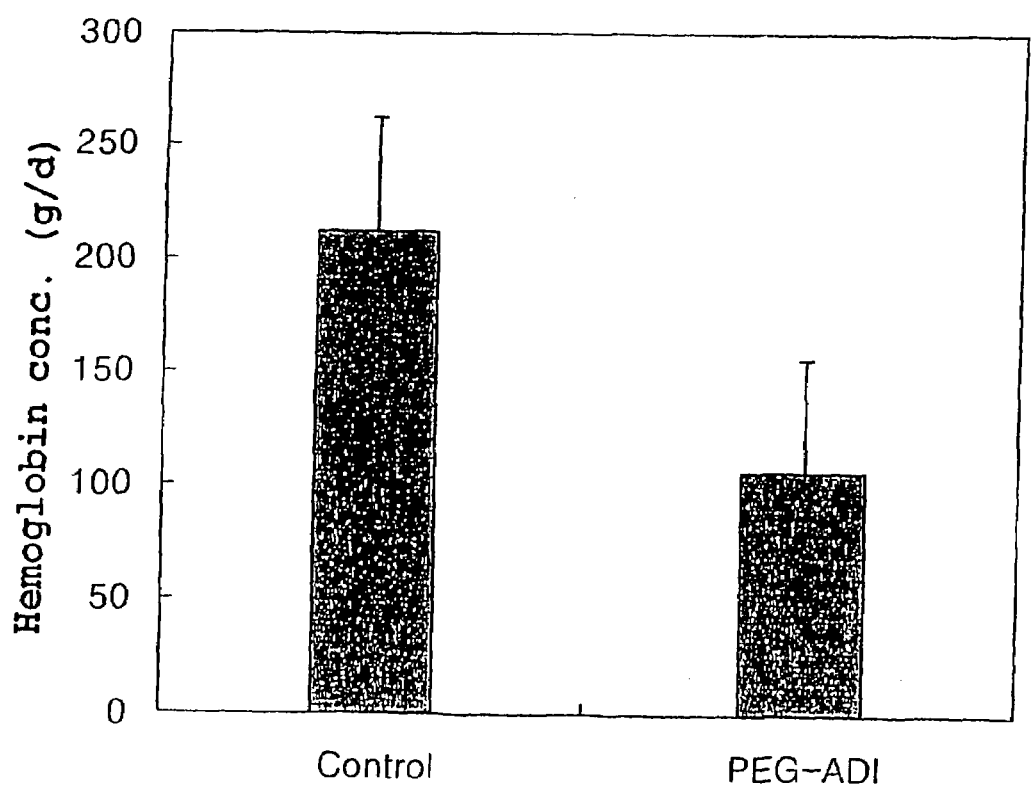
FIG. 15 is a graph showing the inhibitory effect of PEG-arginine deiminase on angiogenesis in the mouse Matrigel model.

The inhibitory effect of PEG-ADI on angiogenesis was quantitatively measured as in Example 6 using the mouse Matrigel model. 2 μg of PEG-ADI was included in the Matrigel and compared with the control group. After 3-5 days, the epidermis was removed and the content of hemoglobin was measured in excised Matrigel. As shown in Table M, experimental group exhibited angiogenesis inhibition to the extent of 50% as compared with the control group (FIG. 15).

---

What is claimed is:

1. A method for inhibiting angiogenesis in a mammal comprising the step of administering arginine deiminase of SEQ ID NO: 10 to the mammal in need thereof in an amount effective to inhibit angiogenesis.

2. The method of claim 1, which is used for treating or inhibiting a disease selected from the group consisting of: angioma, angiofibroma, arthritis, diabetic retinopathy, premature infant's retinopathy, neovascular glaucoma, corneal disease. involutional magula, degeneration of macula, pterygium, retinal degeneration, retrolental fibroplasias, granular conjugativitis, psoriasis, telanglectasls, pyogenic granuloma, sebortheic dermatitis and acne.

3. The method of claim 1, wherein arginine deiminase is obtained from *Mycoplasma arginini*.

4. The method of claim 1, wherein arginine deiminase is a recombinant protein.

5. The method of claim 4, wherein the arginine deiminase is the protein encoded by the polynucleotide sequence of SEQ ID NO: 9.

6. The method of claim 1, wherein the arginine deiminase is conjugated to a polymer.

7. The method of claim 6, wherein the polymer is selected from the group consisting of: polyethylene glycol, polypropylene glycol, polyoxyethylene, polytrimethylene glycol, polylactic acid, polyacrylic acid, polyamino acids, polyurethane, polyphosphazenes, poly[L-lysine], polyalkylene oxide, polysaccharide, dextran, polyvinyl pyrrolidone, polyvinyl alcohol and polyacryl amide.

8. The method of claim 2, wherein the arginine deiminase is obtained from *Mycoplasma arginini*.

9. The method of claim 2, wherein the arginine deiminase is a recombinant protein.

* * * * *

SEQUENCE LISTING

```
<160> NUMBER OF SEQ ID NOS: 10

<210> SEQ ID NO 1
<211> LENGTH: 34
<212> TYPE: DNA
<213> ORGANISM: Artificial Sequence
<220> FEATURE:
<223> OTHER INFORMATION: site-directed mutagenesis product from
      polynucleotide coding Mycoplasma Arginini Arginine Deiminase

<400> SEQUENCE: 1
aaactaatta acaccccgtg gtactacgac cctt                              34

<210> SEQ ID NO 2
<211> LENGTH: 34
<212> TYPE: DNA
<213> ORGANISM: Artificial Sequence
<220> FEATURE:
<223> OTHER INFORMATION: site-directed mutagenesis product from
      polynucleotide coding Mycoplasma Arginini Arginine Deiminase

<400> SEQUENCE: 2
```

-continued aagggtcgta gtaccacggg gtgttaatta gttt                                34

<210> SEQ ID NO 3
<211> LENGTH: 37
<212> TYPE: DNA
<213> ORGANISM: Artificial Sequence
<220> FEATURE:
<223> OTHER INFORMATION: site-directed mutagenesis product from
      polynucleotide coding Mycoplasma Arginini Arginine Deiminase

<400> SEQUENCE: 3
gcaattaacg ttccgaaatg gaccaactta atgcact                             37

<210> SEQ ID NO 4
<211> LENGTH: 37
<212> TYPE: DNA
<213> ORGANISM: Artificial Sequence
<220> FEATURE:
<223> OTHER INFORMATION: site-directed mutagenesis product from
      polynucleotide coding Mycoplasma Arginini Arginine Deiminase

<400> SEQUENCE: 4
agtgcattaa gttggtccat ttcggaacgt taattgc                             37

<210> SEQ ID NO 5
<211> LENGTH: 36
<212> TYPE: DNA
<213> ORGANISM: Artificial Sequence
<220> FEATURE:
<223> OTHER INFORMATION: site-directed mutagenesis product from
      polynucleotide coding Mycoplasma Arginini Arginine Deiminase

<400> SEQUENCE: 5
atgcacttag acacctggct gaccatgtta gacaag                              36

<210> SEQ ID NO 6
<211> LENGTH: 36
<212> TYPE: DNA
<213> ORGANISM: Artificial Sequence
<220> FEATURE:
<223> OTHER INFORMATION: site-directed mutagenesis product from
      polynucleotide coding Mycoplasma Arginini Arginine Deiminase

<400> SEQUENCE: 6
cttgtctaac atggtcagcc aggtgtctaa gtgcat                              36

<210> SEQ ID NO 7
<211> LENGTH: 28
<212> TYPE: DNA
<213> ORGANISM: Artificial Sequence
<220> FEATURE:
<223> OTHER INFORMATION: site-directed mutagenesis product from
      polynucleotide coding Mycoplasma Arginini Arginine Deiminase

<400> SEQUENCE: 7
gtatttaaat tctgggatta tgacttag                                       28

<210> SEQ ID NO 8
<211> LENGTH: 28
<212> TYPE: DNA
<213> ORGANISM: Artificial Sequence
<220> FEATURE:
<223> OTHER INFORMATION: site-directed mutagenesis product from
      polynucleotide coding Mycoplasma Arginini Arginine Deiminase

<400> SEQUENCE: 8
ctaagtcata atcccagaat ttaaatac                                       28

```
<210> SEQ ID NO 9
<211> LENGTH: 1233
<212> TYPE: DNA
<213> ORGANISM: Artificial Sequence
<220> FEATURE:
<223> OTHER INFORMATION: recombinant polynucleotide coding Mycoplasma
      Arginini Arginine Deiminase
<220> FEATURE:
<221> NAME/KEY: CDS
<222> LOCATION: (1)..(1230)

<400> SEQUENCE: 9 atg tct gtg ttt gat agc aaa ttt aaa gga att cac gtt tat tca gaa      48
Met Ser Val Phe Asp Ser Lys Phe Lys Gly Ile His Val Tyr Ser Glu
 1               5                  10                  15 att ggt gaa tta gaa tca gtt cta gtt cac gaa cca gga cgc gaa att      96
Ile Gly Glu Leu Glu Ser Val Leu Val His Glu Pro Gly Arg Glu Ile
             20                  25                  30 gac tat att aca cca gct aga cta gat gaa tta tta ttc tca gct atc     144
Asp Tyr Ile Thr Pro Ala Arg Leu Asp Glu Leu Leu Phe Ser Ala Ile
         35                  40                  45 tta gaa agc cac gat gct aga aaa gaa cac aaa caa ttc gta gca gaa     192
Leu Glu Ser His Asp Ala Arg Lys Glu His Lys Gln Phe Val Ala Glu
 50                  55                  60 tta aaa gca aac gac atc aat gtt gtt gaa tta att gat tta gtt gct     240
Leu Lys Ala Asn Asp Ile Asn Val Val Glu Leu Ile Asp Leu Val Ala
 65                  70                  75                  80 gaa aca tat gat tta gca tca caa gaa gct aaa gat aaa tta atc gaa     288
Glu Thr Tyr Asp Leu Ala Ser Gln Glu Ala Lys Asp Lys Leu Ile Glu
                 85                  90                  95 gaa ttt tta gaa gac tca gaa cca gtt cta tca gaa gaa cac aaa gta     336
Glu Phe Leu Glu Asp Ser Glu Pro Val Leu Ser Glu Glu His Lys Val
            100                 105                 110 gtt gta agg aac ttc tta aaa gct aaa aaa aca tca aga gaa tta gta     384
Val Val Arg Asn Phe Leu Lys Ala Lys Lys Thr Ser Arg Glu Leu Val
        115                 120                 125 gaa atc atg atg gca ggg atc aca aaa tac gat tta ggt atc gaa gca     432
Glu Ile Met Met Ala Gly Ile Thr Lys Tyr Asp Leu Gly Ile Glu Ala
    130                 135                 140 gat cac gaa tta atc gtt gac cca atg cca aac cta tac ttc aca cgt     480
Asp His Glu Leu Ile Val Asp Pro Met Pro Asn Leu Tyr Phe Thr Arg
145                 150                 155                 160 gac cca ttt gca tca gta ggt aat ggt gta aca atc cac tac atg cgt     528
Asp Pro Phe Ala Ser Val Gly Asn Gly Val Thr Ile His Tyr Met Arg
                165                 170                 175 tac aaa gtt aga caa cgt gaa aca tta ttc tca aga ttt gta ttc tca     576
Tyr Lys Val Arg Gln Arg Glu Thr Leu Phe Ser Arg Phe Val Phe Ser
            180                 185                 190 aat cac cct aaa cta att aac acc ccg tgg tac tac gac cct tca cta     624
Asn His Pro Lys Leu Ile Asn Thr Pro Trp Tyr Tyr Asp Pro Ser Leu
        195                 200                 205 aaa tta tca atc gaa ggt gga gac gta ttt atc tac aac aat gac aca     672
Lys Leu Ser Ile Glu Gly Gly Asp Val Phe Ile Tyr Asn Asn Asp Thr
    210                 215                 220 tta gta gtt ggt gtt tct gaa aga act gac tta caa aca gtt act tta     720
Leu Val Val Gly Val Ser Glu Arg Thr Asp Leu Gln Thr Val Thr Leu
225                 230                 235                 240 tta gct aaa agc att gtt gct aat aaa gaa tgt gaa ttc aaa cgt att     768
Leu Ala Lys Ser Ile Val Ala Asn Lys Glu Cys Glu Phe Lys Arg Ile
                245                 250                 255
```

```
gtt gca att aac gtt ccg aaa tgg acc aac tta atg cac tta gac acc      816
Val Ala Ile Asn Val Pro Lys Trp Thr Asn Leu Met His Leu Asp Thr
        260                 265                 270 tgg ctg acc atg tta gac aag gac aaa ttc cta tac tca cca atc gct      864
Trp Leu Thr Met Leu Asp Lys Asp Lys Phe Leu Tyr Ser Pro Ile Ala
            275                 280                 285 aac gac gta ttt aaa ttc tgg gat tat gac tta gta aac ggt gga gca      912
Asn Asp Val Phe Lys Phe Trp Asp Tyr Asp Leu Val Asn Gly Gly Ala
        290                 295                 300 gaa cca caa cca gtt gaa aac gga tta cct cta gaa gga tta tta caa      960
Glu Pro Gln Pro Val Glu Asn Gly Leu Pro Leu Glu Gly Leu Leu Gln
305                 310                 315                 320 tca atc att aac aaa aaa cca gtt cta att cct atc gca ggt gaa ggt     1008
Ser Ile Ile Asn Lys Lys Pro Val Leu Ile Pro Ile Ala Gly Glu Gly
            325                 330                 335 gct tca caa atg gaa atc gaa aga gaa aca cac ttc gat ggt aca aac     1056
Ala Ser Gln Met Glu Ile Glu Arg Glu Thr His Phe Asp Gly Thr Asn
        340                 345                 350 tac tta gca att aga cca ggt gtt gta att ggt tac tca cgt aac gaa     1104
Tyr Leu Ala Ile Arg Pro Gly Val Val Ile Gly Tyr Ser Arg Asn Glu
            355                 360                 365 aaa aca aac gct gct cta gaa gct gca ggc att aaa gtt ctt cca ttc     1152
Lys Thr Asn Ala Ala Leu Glu Ala Ala Gly Ile Lys Val Leu Pro Phe
370                 375                 380 cac ggt aac caa tta tca tta ggt atg ggt aac gct cgt tgt atg tca     1200
His Gly Asn Gln Leu Ser Leu Gly Met Gly Asn Ala Arg Cys Met Ser
385                 390                 395                 400 atg cct tta tca cgc aaa gat gtg aaa tgg tag                          1233
Met Pro Leu Ser Arg Lys Asp Val Lys Trp
            405                 410

<210> SEQ ID NO 10
<211> LENGTH: 410
<212> TYPE: PRT
<213> ORGANISM: Artificial Sequence
<220> FEATURE:
<223> OTHER INFORMATION: Amino acids coding Mycoplasma Arginine
      Deiminase

<400> SEQUENCE: 10

Met Ser Val Phe Asp Ser Lys Phe Lys Gly Ile His Val Tyr Ser Glu
 1               5                  10                  15

Ile Gly Glu Leu Glu Ser Val Leu Val His Glu Pro Gly Arg Glu Ile
                20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Gln Phe Val Ala Glu
        50                  55                  60

Leu Lys Ala Asn Asp Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Lys Val
            100                 105                 110

Val Val Arg Asn Phe Leu Lys Ala Lys Lys Thr Ser Arg Glu Leu Val
        115                 120                 125

Glu Ile Met Met Ala Gly Ile Thr Lys Tyr Asp Leu Gly Ile Glu Ala
    130                 135                 140

Asp His Glu Leu Ile Val Asp Pro Met Pro Asn Leu Tyr Phe Thr Arg
```

-continued

```
            145                 150                 155                 160
Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
                180                 185                 190

Asn His Pro Lys Leu Ile Asn Thr Pro Trp Tyr Tyr Asp Pro Ser Leu
            195                 200                 205

Lys Leu Ser Ile Glu Gly Gly Asp Val Phe Ile Tyr Asn Asn Asp Thr
            210                 215                 220

Leu Val Val Gly Val Ser Glu Arg Thr Asp Leu Gln Thr Val Thr Leu
225                 230                 235                 240

Leu Ala Lys Ser Ile Val Ala Asn Lys Glu Cys Glu Phe Lys Arg Ile
                245                 250                 255

Val Ala Ile Asn Val Pro Lys Trp Thr Asn Leu Met His Leu Asp Thr
                260                 265                 270

Trp Leu Thr Met Leu Asp Lys Asp Lys Phe Leu Tyr Ser Pro Ile Ala
            275                 280                 285

Asn Asp Val Phe Lys Phe Trp Asp Tyr Asp Leu Val Asn Gly Gly Ala
            290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
            355                 360                 365

Lys Thr Asn Ala Ala Leu Glu Ala Ala Gly Ile Lys Val Leu Pro Phe
            370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410
```